United States Patent
Mocnik et al.

(10) Patent No.: US 11,141,417 B2
(45) Date of Patent: Oct. 12, 2021

(54) VORICONAZOLE INCLUSION COMPLEXES

(71) Applicant: XELLIA PHARMACEUTICALS APS, Copenhagen (DK)

(72) Inventors: Anita Bevetek Mocnik, Sesvetski Kraljevec (HR); Ivona Jasprica, Zagreb (HR); Sasa Grubesic, Zagreb (HR)

(73) Assignee: XELLIA PHARMACEUTICALS APS, Copenhagen S (DK)

(*) Notice: Subject to any disclaimer, the term of this patent is extended or adjusted under 35 U.S.C. 154(b) by 0 days.

(21) Appl. No.: 16/256,703

(22) Filed: Jan. 24, 2019

(65) Prior Publication Data

US 2019/0183891 A1 Jun. 20, 2019

Related U.S. Application Data

(63) Continuation of application No. 14/760,260, filed as application No. PCT/EP2014/050328 on Jan. 9, 2014.

(60) Provisional application No. 61/751,394, filed on Jan. 11, 2013.

(51) Int. Cl.
| | |
|---|---|
| *A61K 31/506* | (2006.01) |
| *A61K 9/08* | (2006.01) |
| *C08L 5/16* | (2006.01) |
| *C08B 37/16* | (2006.01) |
| *A61K 47/69* | (2017.01) |
| *A61K 9/19* | (2006.01) |
| *B82Y 5/00* | (2011.01) |

(52) U.S. Cl.
CPC .......... *A61K 31/506* (2013.01); *A61K 9/08* (2013.01); *A61K 9/19* (2013.01); *A61K 47/6951* (2017.08); *B82Y 5/00* (2013.01); *C08B 37/0012* (2013.01); *C08B 37/0015* (2013.01); *C08L 5/16* (2013.01)

(58) Field of Classification Search
CPC .... A61K 31/506; A61K 47/6951; A61K 9/08; C08B 37/0012; C08B 37/0015; C08L 5/16
See application file for complete search history.

(56) References Cited

U.S. PATENT DOCUMENTS

| | | |
|---|---|---|
| 6,632,803 B1 | 10/2003 | Harding |
| 2012/0065255 A1 | 3/2012 | Palepu |
| 2015/0352112 A1 | 12/2015 | Mocnik et al. |

FOREIGN PATENT DOCUMENTS

| | | | |
|---|---|---|---|
| CN | 1788725 A | | 6/2006 |
| CN | 101849905 A | | 10/2010 |
| CN | 102058519 A | | 5/2011 |
| EP | 2018866 A1 | * | 1/2009 |
| EP | 2018866 A1 | | 1/2009 |
| EP | 2409699 A1 | | 1/2012 |
| WO | 2011020605 A1 | | 2/2011 |
| WO | WO2011020605 A1 | * | 2/2011 |
| WO | 2011079969 A1 | | 7/2011 |
| WO | 2012171561 A1 | | 12/2012 |
| WO | WO2012171561 A1 | * | 12/2012 |

OTHER PUBLICATIONS 1.132 Declaration of Valerie Denise Harding; signed Jul. 23, 2002; from U.S. Appl. No. 09/402,289 file history; pp. 1-6.
Buchanan et al.; "Solubility and Dissolution Studies of Antifungal Drug:hydroxybutenyl-B-cyclo-dextrin Complexes"; Cellulose; 2007; vol. 14; pp. 35-47.
CAVASOL W7 HP Pharma, Product Information Sheet, info. finechemicals@wacker.com; www.wacker.com; pp. 1-2; Version 4.00 (2005).
ICH Harmonised Tripartite Guideline Stability Testing of New Drug Substances and Products Q1A(R2); International Conference on Harmonisation of Technical Requirements for Registration of Pharmaceuticals for Human Use, Current Step 4 version, dated Feb 6, pp. 1-23, 2003.
International Search Report and Written Opinion; International Application No. PCT/EP2014/050328; International Filing Date Jan. 9, 2014; dated Mar. 24, 2014; 10 pages.
Pharmaceutical Formulation Containing Voriconazole; Retrieved from the internet: URL:http://ip.com/IPCOM/000172823> [retrieved on Jul. 16, 2008]; pp. 1-2.
Aechter, B.; "Response to Official Communication Pursuant to Article 94(3) EPC"; European Patent Application No. 10745177.5 Prosecution Communication; dated 2014; 3 pages.
Traegler-Goeldel, M.; "Official Communication Pursuant to Article 94(3) EPC"; European Patent Application No. 10745177.5 Prosecution Communication; dated 2014; 5 pages.

* cited by examiner

*Primary Examiner* — Bahar Craigo
(74) *Attorney, Agent, or Firm* — Cantor Colburn LLP

(57) ABSTRACT

Described are voriconazole formulations including 2-hydroxypropyl-β-cyclodextrins and the preparation thereof.

19 Claims, No Drawings

VORICONAZOLE INCLUSION COMPLEXES

CROSS-REFERENCE TO RELATED APPLICATIONS

This application is a continuation of U.S. application Ser. No. 14/760,260, filed on Jul. 10, 2015, which is a § 371 of PCT/EP2014/050328 filed Jan. 9, 2014 which claims the benefit of priority to U.S. provisional application No. 61/751,394, filed on Jan. 11, 2013, under the provisions of 35 U.S.C. § 119 and the International Convention for the protection of Industrial Property, which are incorporated herein by reference.

BACKGROUND

Voriconazole is a triazole antifungal agent with structural formula:

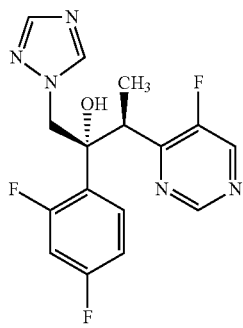 [SMILES: C[C@@H](c1ncncc1F)[C@](O)(Cn1cncn1)c1ccc(F)cc1F]

Voriconazole is designated chemically as (2R,3S)-2-(2,4-difluorophenyl)-3-(5-fluoro-4-pyrimidinyl)-1-(1H-1,2,4triazol-1-yl)-2-butanol with an empirical formula of $C_{16}H_{14}F_3N_5O$ and a molecular weight of 349.3.

Voriconazole contains a triazole functionality and is a single diastereomer with two reported pKa values of 4.98 and 12.0. Voriconazole is a weak base; it is not hygroscopic and is classified as having a low solubility (very slightly soluble in water), and being a high permeability compound (BCS class II).

Voriconazole is a chiral antifungal agent belonging to the class of triazole antifungals. The reference drug product is marketed in Europe and US under the trade name Vfend® by Pfizer. The drug is indicated for the treatment of invasive aspergillosis (*Aspergillus fumigatus*) and esophageal candidiasis (*Candidia albicans*), as well as infections caused by *Scedosporium apiospermum* and *Fusarium* spp.

The prior art implies that Voriconazole is not a stable molecule—it degrades in water, it is susceptible to oxidative degradation and decomposes in acidic and basic media. Photodegradation occurs under severe light stress conditions and it degrades greatly under elevated temperature.

Specified degradation products of voriconazole are identified as:

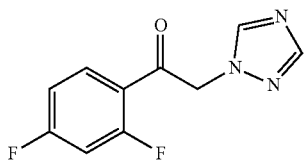 [SMILES: O=C(Cn1cncn1)c1ccc(F)cc1F]

1-(2,4-difluorophenyl)-2-(1H-1,2,4-triazol-1-yl) ethanone,

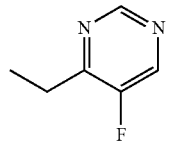

4-ethyl-5-fluoropyrimidine,

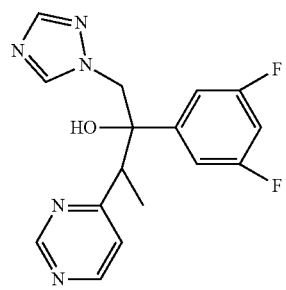 [SMILES: CC(c1ccncn1)C(O)(Cn1cncn1)c1cc(F)cc(F)c1]

((2RS, 3 SR)-2-(2,4-difluorophenyl)-3-(pyrimidin-4-yl)-1-(1H-1,2,4-triazol-1-yl)butan-2-ol) and enantiomer, and

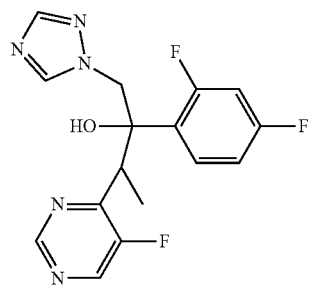 [SMILES: CC(c1ncncc1F)C(O)(Cn1cncn1)c1ccc(F)cc1F]

(2RS,3RS)-2-(2,4-difluorophenyl)-3-(5-fluoropyrimidin-4-yl)-1-(1H-1,2,4-triazol-1-yl)butan-2-ol (voriconazole enantiomer).

Voriconazole is semi-polar in nature which means that it is generally not solubilized by conventional means such as oils, surfactants or water miscible co-solvents. The voriconazole drug substance is a white to off white powder in solid state.

In order to obtain water a soluble formulation of voriconazole that is suitable for administration by intravenous infusion, the solubility of the active compound has to be enhanced. 2-hydroxypropyl-β-cyclodextrin has been used for that purpose and the basis for its usage is the ability of 2-hydroxypropyl-β-cyclodextrin to interact with poorly water-soluble voriconazole resulting in an increase in its apparent water solubility. The mechanism for this solubilization is rooted in the ability of 2-hydroxypropyl-β-cyclodextrin to form non-covalent dynamic inclusion complexes in a solution, in which the guest and host molecules are in dynamic equilibrium with the complex.

U.S. Pat. No. 6,632,803 provides a pharmaceutical formulation comprising voriconazole, or a pharmaceutically acceptable salt thereof, and a sulfobutylether ☐-cyclodextrin.

EP 2 018 866 discloses a process for improving the solubility of voriconazole in aqueous solutions comprising voriconazole and a beta-cyclodextrin.

WO 2012/171561 discloses a process for improving the stability of voriconazole in pharmaceutical compositions comprising voriconazole and a beta-cyclodextrin, wherein the said composition comprises a stabilizing amount of lactose.

The marketed Voriconazole lyophilized formulation (Vfend®) contains 200 mg of voriconazole and is intended for reconstitution with Water for Injection to obtain a solution containing 10 mg/mL of Voriconazole and 160 mg/mL of sulfobutyl-ether beta-cyclodextrin. The resultant solution is further diluted prior to administration as an intravenous infusion.

SUMMARY OF THE INVENTION

The present invention provides new voriconazole formulations comprising 2-hydroxypropyl-β-cyclodextrins. The invention is inter alia based on the discovery that formulations comprising voriconazole are stabilized when formulated using 2-hydroxy-β-propyl-cyclodextrin within a certain range of molar substitution.

According to one embodiment of the present invention, a stabilized pharmaceutical formulation is thus provided comprising voriconazole and a substituted β-cyclodextrin characterized by a molar substitution of the β-cyclodextrin by hydroxypropyl groups of more than 0.8, provided that the formulation does not comprise lactose.

According to another embodiment, the pharmaceutical formulation of the present invention comprises substituted β-cyclodextrins wherein the substituent on the β-cyclodextrin is a 2-hydroxypropyl group.

In one embodiment of the present invention, the molar substitution of the 2-hydroxypropyl β-cyclodextrin is 0.8-1.1, preferably 0.8-1.0. According to yet another embodiment, the molar substitution of the 2-hydroxypropyl β-cyclodextrin is 0.9.

According to another embodiment of the present invention, the said stabilized pharmaceutical formulation has a pH in the range of about 4-7.

According to a further embodiment, the pharmaceutical formulation according to the present invention further comprises a pH adjusting agent.

According to a further embodiment, the pharmaceutical formulation according to the present invention further comprises an acidification agent.

According to a further embodiment, the pharmaceutical formulation according to the present invention further comprises organic carboxylic acids.

According to a further embodiment, the pharmaceutical formulation according to the present invention further comprises citrate, acetate, tartrate and/or succinate buffers.

According to a further embodiment, the pharmaceutical formulation according to the present invention further comprises citric, acetic, tartaric and/or succinic acids.

According to yet another aspect of the present invention, the pharmaceutical formulation according to the above mentioned invention is further lyophilized.

The present pharmaceutical formulation may comprise about 4-10% w/w voriconazole in solid state, such as about 6% w/w voriconazole in solid state.

Furthermore, the present pharmaceutical formulation may comprise about 90-96% w/w β-cyclodextrin in solid state, such as e.g. about 94% w/w β-cyclodextrin in solid state.

According to yet another aspect of the present invention, the formulation comprises voriconazole and 2-hydroxypropyl-3-cyclodextrin in a molar ratio of up to 1:5.

According to a another embodiment of the present invention, the formulation comprises voriconazole and 2-hydroxypropyl-β-cyclodextrin in a molar ratio of 1:2 to 1:5

According to the most preferred embodiment of the present invention, the formulation comprises voriconazole and 2-hydroxypropyl-β-cyclodextrin in a molar ratio of 1:3.6

According to a preferred embodiment of the present invention, the formulation in solid state comprises voriconazole and 2-hydroxypropyl-β-cyclodextrin in a weight ratio of 1:22 to 1:10.

According to a preferred embodiment of the present invention, the formulation in solid state comprises voriconazole and 2-hydroxypropyl-β-cyclodextrin in a weight ratio of 1:18 to 1:14.

According to a preferred embodiment of the present invention, the formulation in solid state comprises voriconazole and 2-hydroxypropyl-β-cyclodextrin in a weight ratio of 1:16.

According to another aspect of the present invention, a reconstituted formulation is provided consisting of a solution comprising a stabilized pharmaceutical formulation according to the present invention being dissolved in a diluent suitable for injection or intravenous infusion.

The reconstituted formulation according to the present invention may comprise 1-20 mg/ml voriconazole.

The reconstituted formulation according to the present invention may comprise 50-300 mg/ml 2-hydroxypropyl-3-cyclodextrin.

According to yet another aspect of the present invention, a stabilized pharmaceutical formulation is provided, consisting of:
  i. voriconazole;
  ii. a substituted β-cyclodextrin characterized by a molar substitution of the β-cyclodextrin by 2-hydroxypropyl groups of more than 0.8;
  iii. optionally pH adjusting agents; and
  iv. optionally pharmaceutically acceptable diluents or solvents.

The pH of said formulation is preferably within the range of about 4-7.

The present inventors have also found that a stabilizing effect is achieved by keeping the pH within a certain range when formulating voriconazole formulation comprising substituted β-cyclodextrin. Thus, according to yet another aspect of the present invention, a stabilized pharmaceutical is provided comprising voriconazole and a substituted β-cyclodextrin, wherein the compositions has pH of 4-7 when dissolved in a suitable diluent.

According to a further embodiment of this aspect, the pharmaceutical formulation according to the present invention further comprises a pH adjusting agent.

According to yet a further embodiment, the pharmaceutical formulation according to the present invention further comprises an acidification agent.

According to yet a further embodiment, the pharmaceutical formulation according to the present invention further comprises organic carboxylic acids.

According to yet a further embodiment, the pharmaceutical formulation according to the present invention further comprises citrate, acetate, tartrate and/or succinate buffers.

According to yet a further embodiment, the pharmaceutical formulation according to the present invention further comprises citric, acetic, tartaric and/or succinic acids.

It is to be understood that said formulation, based on the findings of the stabilizing effect of the pH, may be further lyophilized and reconstituted similar to the other embodiments of the present invention.

The present applications furthermore provide a method for stabilizing a composition comprising voriconazole, wherein the method comprises the steps of:
 a. providing an aqueous solution of 2-hydroxypropyl-β-cyclodextrin having a molar substitution of the β-cyclodextrin by hydroxypropyl groups of more than 0.8;
 b. adding voriconazole;
 c. optionally adjusting the pH; and
 d. optionally lyophilizing the obtained stabilized composition.

According to one embodiment of the present method, the prepared composition does not comprise lactose.

Finally, the present application provides the use of a substituted β-cyclodextrin having a molar substitution of the β-cyclodextrin by hydroxypropyl groups of more than 0.8 as an agent for stabilization of a composition comprising voriconazole.

DETAILED DESCRIPTION OF THE INVENTION

Voriconazole is only sparingly soluble in water. Without being bound by theory, it is believed that 2-hydroxypropyl-substituted β-cyclodextrin can form inclusion complex with voriconazole and thus increase its aqueous solubility. Further, such voriconazole complexes are more stable in aqueous media than voriconazole itself.

Furthermore, data from the literature imply that voriconazole is unstable in alkaline media, where it degrades quickly especially when it is exposed to elevated temperatures. Available data also imply that pH of the media can have an impact on the stability of voriconazole formulations.

Cyclodextrins are a group of structurally related natural products formed by bacterial digestion of cellulose. These cyclic oligosaccharides consist of (α-1,4)-linked α-D-glucopyranose units and contain a somewhat lipophilic central cavity and a hydrophilic outer surface. Due to the chair conformation of the glucopyranose units, the cyclodextrins are shaped like a truncated cone rather than perfect cylinders. The hydroxyl functions are orientated to the cone exterior with the primary hydroxyl groups of the sugar residues at the narrow edge of the cone and the secondary hydroxyl groups at the wider edge. The central cavity is lined by the skeletal carbons and ethereal oxygens of the glucose residues, which gives it a lipophilic character. The polarity of the cavity has been estimated to be similar to that of an aqueous ethanolic solution. The natural α-, β- and γ-cyclodextrin consist of six, seven, and eight glucopyranose units, respectively. Cyclodextrin derivatives of pharmaceutical interest include the hydroxypropyl derivatives of β- and γ-cyclodextrin, the randomly methylated β-cyclodextrin, sulfobutylether β-cyclodextrin, and the so-called branched cyclodextrins such as glucosyl-β-cyclodextrin.

In aqueous solutions cyclodextrins are able to form inclusion complexes with many drugs by taking up a drug molecule or more frequently some lipophilic moiety of the molecule, into the central cavity. No covalent bonds are formed or broken during the complex formation and drug molecules in the complex are in rapid equilibrium with free molecules in the solution. The driving forces for the complex formation include release of enthalpy-rich water molecules from the cavity, electrostatic interactions, van der Waals interactions, hydrophobic interactions, hydrogen bonding, and release of conformational strain and charge-transfer interactions.

In the pharmaceutical industry cyclodextrins have mainly been used as complexing agents to increase aqueous solubility of poorly soluble drugs, and to increase their bioavailability and stability.

Although the natural CDs and their complexes are hydrophilic, their aqueous solubility can be rather limited, especially in the case of βCD. This is thought to be due to relatively strong binding of the CD molecules in the crystal state (i.e. relatively high crystal lattice energy). Random substitution of hydroxyl groups, even by hydrophobic moieties such as methoxy functions, will result in dramatic improvements in their solubility. Moreover, some derivatives, such as 2-hydroxypropyl (HPβCD and HPγCD) and sulfobutylether (SBEβCD), possess improved toxicological profiles in comparison to their parent CDs.

The Degree of Substitution of cyclodextrin (DS) is defined as the average number of substituted hydroxyl groups per glucopyranose unit of CD ring. Since the number of reactive hydroxyls per mole of glucopyranose unit is 3, the maximum numbers of substituents possible for α-, β-, and γ-CDs are 18, 21, and 24, respectively.

Another term used to describe cyclodextrin substitution is molar substitution (MS). This term, as used in this specification, describes the average number of moles of the substituting agent, e.g, hydroxypropyl, per mole of glucopyranose. For example when a hydroxypropyl-β-cyclodextrin has DS=14, the MS is 14/7 or 2. Thus, the "molar substitution of the β-cyclodextrin by hydroxypropyl groups", as used in this specification, means the average number of hydroxypropyl substituents attached to each glucopyranose unit in the cyclodextrin.

Pharmaceutical formulation, as used in this specification, means any formulation intended for therapeutic or prophylactic treatment. Pharmaceutical formulations according to the present invention can be in solid or liquid state.

β-cyclodextrin, as used in this specification, means any cyclodextrin comprising 7 (α-1,4)-linked α-D-glucopyranose units, e.g.

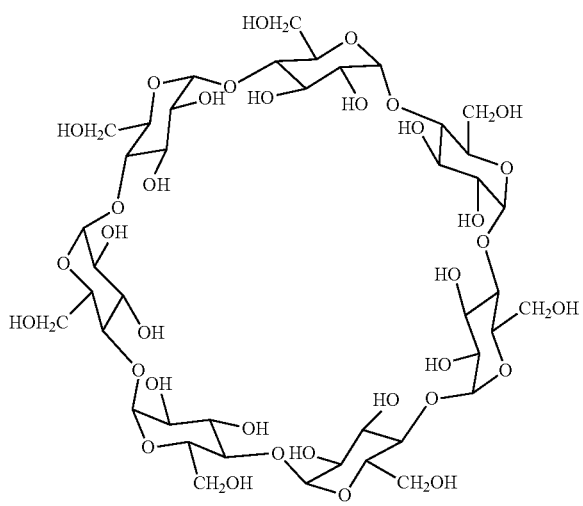 [SMILES: OCC1OC2OC3C(CO)OC(OC4C(CO)OC(OC5C(CO)OC(OC6C(CO)OC(OC7C(CO)OC(OC8C(CO)OC(OC1C(O)C2O)C(O)C8O)C(O)C7O)C(O)C6O)C(O)C5O)C(O)C4O)C(O)C3O]

Hydroxypropyl-β-cyclodextrin, as used in this specification, means any β-cyclodextrin monomer comprising at least one hydroxypropyl substituent attached to a hydroxyl group on the cyclodextrin. Hydroxypropyl-β-cyclodextrin is abbreviated as HPβCD.

The hydroxypropyl substituent as used in this specification is meant to embrace several different substituents including:

—CH₂—CH₂—CH₂OH
—CH₂—CHOH—CH₃
—CHOH—CH₂—CH₃
—CHOH—CHOH—CH₃
—CHOH—CH₂—CH₂OH
—CH₂—CHOH—CH₂OH
—CHOH—CHOH—CH₂OH

One example of a hydroxypropyl-3-cyclodextrin could be represented:

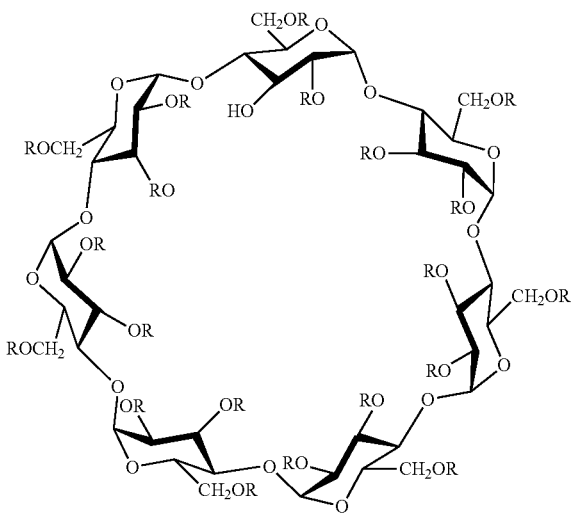

wherein R=—CH₂—CH₂—CH₂OH 2-hydroxypropyl-β-cyclodextrin, as used in this specification, means any β-cyclodextrin monomer comprising at least one 2-hydroxypropyl substituent attached to a hydroxyl group on the β-cyclodextrin. 2-hydroxypropyl-β-cyclodextrin is abbreviated 2-HPβCD. One example of a 2-hydroxypropyl-β-cyclodextrin could be represented as on the following figure:

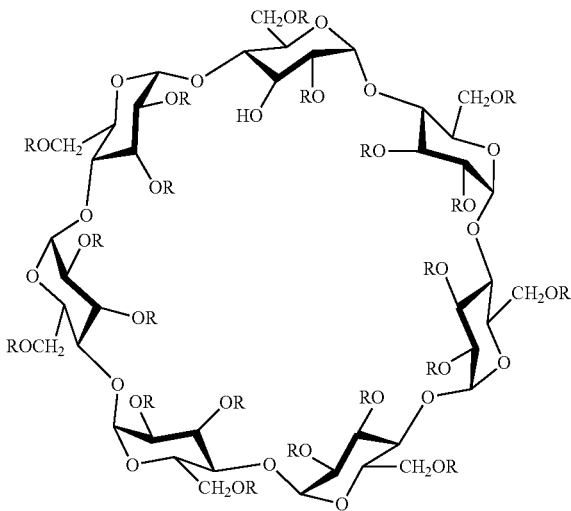

wherein R=—CH₂—CHOH—CH₃.

Whenever pH is mentioned in respect of a formulation according to the present invention, e.g. in respect of formulation having a pH within a specified range, it is to be understood that the formulation is in liquid form if not otherwise stated. "pH of 3-8" is meant to include pH 8.0, pH 7.5, 7.0, pH 6.5, pH 3.0. Further included is any pH between any of these; e.g. pH 5.23, pH 3.35, pH 7.39 etc.

"pH of 4-7" is meant to include pH 4.0, pH 5.5, pH 6.0, pH 7.0. Further included is any pH between any of these; e.g. pH 4.23, pH 5.35, pH 5.39 etc.

"Water for injection" as used herein is substantially pure and sterile water, e.g. water purified by distillation or a purification process that is equivalent or superior to distillation in the removal of chemicals and microorganisms. "Ultrapure water" is water with conductivity below 0.055 μS and pH in the range from 5.0 to 7.0 and is used in the following examples as a substitute for "water for injection".

"Stabilizing effect" as used herein is a reduction of the level of impurities in solid or liquid formulations formulated according to the parameters described in the claims, in comparison to the formulations which are not manufactured within the same parameters.

"Stabilized pharmaceutical formulations" are formulations in which voriconazole degrades in lower extent when formulations are exposed to stability testing at elevated temperature in comparison to the non-stabilized formulations in which decomposition of voriconazole is greater under the same stability testing conditions.

EXAMPLES

The voriconazole formulations were prepared in the following manner: first 2-hydroxypropyl-β-cyclodextrin was dissolved in the appropriate vehicle in concentration of 160 mg/mL and then voriconazole was added to the solution in a concentration of 10 mg/mL. After preparation, liquid formulations were filled in vials and subsequently lyophilized.

The following hydroxypropyl beta cyclodextrins were used for preparation of voriconazole formulations:

1. 2-hydroxypropyl-β-cyclodextrin with molar substitution=0.65
2. 2-hydroxypropyl-β-cyclodextrin with molar substitution=0.63
3. 2-hydroxypropyl-β-cyclodextrin with molar substitution=0.87

All formulations were analyzed immediately after lyophilization and then subjected to stability testing at the elevated temperature (40° C.±2° C./75%±5% RH). Analyses of formulations were done at defined time points and during the storage finished product vials were kept in inverted position.

Except pH, content of impurities was analyzed at each specified time point using validated HPLC methods.

The results of the study and conclusions are presented in text and Tables that follow.

Example 1

The composition was prepared according to the above described procedure and as a vehicle ultrapure water was used. Stability of finished product was tested at 40° C./75% RH in inverted position (taken as a worst case) during 1 month. The results are shown in Table 1.

Table 1. Impurity profile and respective pH values of Voriconazole and 2-hydroxypropyl-β-cyclodextrin formulation prepared using 2-hydroxypropyl-β-cyclodextrin of molar substitution equal to 0.65 (ultrapure water was used as solvent).

TABLE 1

| | Formulation: Voriconazole and 2-hydroxypropyl-β-cyclodextrin formulation (MS of 2HPβCD = 0.65) in Ultrapure water Storage Condition: | | |
|---|---|---|---|
| TESTS | START | 2 weeks 40° C./ 75% RH IP | 1 month 40° C./ 75% RH IP |
| pH | 8.9 | 8.6 | 8.6 |
| Related substances (%) | | | |
| 1-(2,4-difluorophenyl)-2-(1H-1,2,4-triazol-1-yl)ethanone | 0.08 | 1.2 | 1.8 |
| 4-ethyl-5-fluoropyrimidine | 0.07 | 1.2 | 1.9 |
| ((2RS,3SR)-2-(2,4-difluorophenyl)-3-(pyrimidin-4-yl)-1-(1H-1,2,4-triazol-1-yl)butan-2-ol) | <LOQ | <LOQ | <LOQ |
| (2RS,3RS)-2-(2,4-Difluorophenyl)-3-(5-fluoropyrimidin-4-yl)-1-(1H-1,2,4-triazol-1-yl)butan-2-ol | <LOQ | 0.30 | 0.45 |
| Total Impurities | 0.20 | 2.6 | 4.2 |

Total impurities = sum of specified and unspecified impurities

From above presented results it can be seen that found level of impurities after two weeks of storage at 40° C./75% RH was rather high. Obtained pH values measured in all samples was in the range from 8.6 to 8.9, which implies that pH of formulation higher than 8 destabilizes the active compound.

Example 2

The compositions were prepared according to the above described procedure, and as a vehicle different buffers were used. The stability of finished products was tested at 40° C./75% RH in inverted position (taken a s a worst case) during 1 month. The results are shown in Table 2.

Table 2. Impurity profiles and respective pH values of voriconazole and 2-hydroxypropyl-β-cyclodextrin formulations prepared using 2-hydroxypropyl-β-cyclodextrin of molar substitution equal to 0.65 dissolved in different buffers with pH value adjusted in the range from 3.8 to 7.2 subjected to stability testing at elevated temperature.

TABLE 2

| | Formulation: | | | | | | | | |
|---|---|---|---|---|---|---|---|---|---|
| | Voriconazole and 2-hydroxypropyl-β-cyclodextrin formulation (MS of 2-HβCD = 0.65) in Citrate buffer with pH adjusted to 7.2 | | | Voriconazole and 2-hydroxypropyl-β-cyclodextrin formulation (MS of 2-HβCD = 0.65) in Citrate buffer with pH adjusted to 5.5 | | | Voriconazole and 2-hydroxypropyl-β-cyclodextrin formulation (MS of 2-HβCD = 0.65) in Citrate buffer with pH adjusted to 3.8 | | |
| | Storage Condition: | | | | | | | | |
| TESTS | START | 2 weeks* | START | 2 weeks* | 1 month** | START | 2 weeks* | 1 month** |
| pH | 7.4 | 7.3 | 5.7 | 5.7 | 5.8 | 4.1 | 4.1 | 4.1 |
| Related substances (%) | | | | | | | | |
| 1-(2,4-difluorophenyl)-2-(1H-1,2,4-triazol-1-yl)ethanone | 0.06 | 1.8 | <LOQ | 0.19 | 0.43 | <LOQ | 0.20 | 0.46 |
| 4-ethyl-5-fluoropyrimidine | 0.06 | 1.9 | <LOQ | 0.19 | 0.40 | <LOQ | 0.21 | 0.42 |

TABLE 2-continued

| | | | | | | | | |
|---|---|---|---|---|---|---|---|---|
| ((2RS,3SR)-2-(2,4-difluorophenyl)-3-(pyrimidin-4-yl)-1-(1H-1,2,4-triazol-1-yl)butan-2-ol) | <LOQ | <LOQ | <LOQ | <LOQ | <LOQ | <LOQ | <LOQ | 0.05 |
| (2RS,3RS)-2-(2,4-Difluorophenyl)-3-(5-fluoropyrimidin-4-yl)-1-(1H-1,2,4-triazol-1-yl)butan-2-ol | <LOQ | 0.49 | <LOQ | 0.05 | 0.11 | <LOQ | <LOQ | 0.07 |
| Total Impurities | 0.17 | 4.2 | 0.05 | 0.47 | 0.98 | <LOQ | 0.45 | 1.0 |

| | Formulation: | | | | | |
|---|---|---|---|---|---|---|
| | Voriconazole and 2-hydroxypropyl-β-cyclodextrin formulation (MS of 2-HβCD = 0.65) in Succinate buffer with pH adjusted to 4.0 | | | Voriconazole and 2-hydroxypropyl-β-cyclodextrin formulation (MS of 2-HβCD = 0.65) in Tartarate buffer with pH adjusted to 4.8 | | |
| | Storage Condition: | | | | | |
| TESTS | START | 2 weeks* | 1 month** | START | 2 weeks* | 1 month** |
| pH | 4.3 | 4.3 | 4.3 | 5.0 | 5.0 | 5.0 |
| Related substances (%) | | | | | | |
| 1-(2,4-difluorophenyl)-2-(1H-1,2,4-triazol-1-yl)ethanone | <LOQ | 0.17 | 0.40 | <LOQ | 0.16 | 0.37 |
| 4-ethyl-5-fluoropyrimidine | <LOQ | 0.18 | 0.37 | <LOQ | 0.17 | 0.35 |
| ((2RS,3SR)-2-(2,4-difluorophenyl)-3-(pyrimidin-4-yl)-1-(1H-1,2,4-triazol-1-yl)butan-2-ol) | <LOQ | <LOQ | <LOQ | <LOQ | <LOQ | 0.05 |
| (2RS,3RS)-2-(2,4-Difluorophenyl)-3-(5-fluoropyrimidin-4-yl)-1-(1H-1,2,4-triazol-1-yl)butan-2-ol | <LOQ | <LOQ | 0.06 | <LOQ | <LOQ | 0.09 |
| Total Impurities | <LOQ | 0.40 | 0.90 | <LOQ | 0.44 | 0.91 |

Total impurities = sum of specified and unspecified impurities

From obtained results in could be concluded that found level of impurities in formulations with pH adjusted in the range from 3.8 to 5.5 are approximately four times lower than in the voriconazole formulation that was prepared using 2-hydroxypropyl-β-cyclodextrin of molar substitution equal to 0.65 dissolved only in ultrapure water (for comparison please see Table 1). Formulation prepared with citrate buffer and pH adjusted to 7.2 showed significant degradation of active compound when exposed to elevated temperature, implying that formulation is destabilized in slightly alkaline media Example 3

The compositions were prepared according to the above described procedure, and as a vehicle ultrapure water was used. Stability of finished products was tested at 40° C./75% RH in inverted position (taken as a worst case) during 2 weeks. The results are shown in Table 3.

Table 3. Impurity profiles and respective pH values of Voriconazole and 2-hydroxypropyl-β-cyclodextrin formulations prepared using 2-hydroxypropyl-β-cyclodextrin of molar substitution equal to 0.87 or 0.63 dissolved in ultrapure water and subjected to stability testing at elevated temperature.

TABLE 3

| | Formulation: | | | |
| --- | --- | --- | --- | --- |
| | Voriconazole and 2-hydroxypropyl-β-cyclodextrin formulation (MS of 2-HPβCD = 0.87) in Ultrapure water | | Voriconazole and 2-hydroxypropyl-β-cyclodextrin formulation (MS of 2-HPβCD = 0.63) in Ultrapure water | |
| | Storage Condition: | | | |
| TESTS | START | 2 weeks 40° C./ 75% RH IP | START | 2 weeks 40° C./ 75% RH IP |
| pH | 6.9 | 7.2 | 7.1 | 7.3 |
| | Related substances (%) | | | |
| 1-(2,4-difluorophenyl)-2-(1H-1,2,4-triazol-1-yl)ethanone | <LOQ | 0.22 | <LOQ | 0.43 |
| 4-ethyl-5-fluoro-pyrimidine | <LOQ | 0.20 | <LOQ | 0.39 |
| ((2RS,3SR)-2-(2,4-difluorophenyl)-3-(pyrimidin-4-yl)-1-(1H-1,2,4-triazol-1-yl)butan-2-ol) | <LOQ | <LOQ | <LOQ | <LOQ |
| (2RS,3RS)-2-(2,4-Difluorophenyl)-3-(5-fluoropyrimidin-4-yl)-1-(1H-1,2,4-triazol-1-yl)butan-2-ol | <LOQ | 0.05 | <LOQ | 0.11 |
| Total Impurities | <LOQ | 0.47 | <LOQ | 0.93 |

Total impurities = sum of specified and unspecified impurities

Obtained results imply that formulation with 2-HPβCD with higher MS is more stable than the formulation with lower MS, as the level of impurities is twice higher in formulation containing 2-HPβCD with lower molar substitution.

Example 4

The composition was prepared according to the above described procedure, and as a vehicle ultrapure water was used. Stability of finished product was tested at 40° C./75% RH in inverted position (taken as a worst case) during 3 months. The results are shown in Table 4.

Table 4. Impurity profiles and respective pH values of Voriconazole and 2-hydroxypropyl-β-cyclodextrin formulation prepared using 2-hydroxypropyl-β-cyclodextrin of molar substitution equal to 0.87 dissolved in ultrapure water and subjected to stability testing at elevated temperature.

TABLE 4

| TESTS | Formulation: Voriconazole and 2-hydroxypropyl-β-cyclodextrin formulation (MS of 2-HPβCD = 0.87) in Ultrapure water Storage Condition: | | |
|---|---|---|---|
| | START | 1 M 40° C./75% RH IP | 3 M 40° C./75% RH IP |
| pH | 6.5 | 6.4 | 6.4 |
| Related substances (%) | | | |
| 1-(2,4-difluorophenyl)-2-(1H-1,2,4-triazol-1-yl)ethenone | <LOD | 0.35 | 0.91 |
| 4-ethyl-5-fluoropyrimidine | <LOD | 0.36 | 0.65 |
| ((2RS,3SR)-2-(2,4-difluorophenyl)-3-(pyrimidin-4-yl)-1-(1H-1,2,4-triazol-1-yl)butan-2-ol) | <LOD | <LOQ | <LOQ |
| (2RS,3RS)-2-(2,4-Difluorophenyl)-3-(5-fluoropyrimidin-4-yl)-1-(1H-1,2,4-triazol-1-yl)butan-2-ol | <LOQ | 0.10 | 0.15 |
| Total Impurities | 0.05 | 0.87 | 1.8 |

Total impurities = sum of specified and unspecified impurities

Example 5

The compositions were prepared according to the above described procedure, and as a vehicle different buffers were used. The stability of finished products was tested at 40° C./75% RH in inverted position (taken as a worst case) during 3 months. The results are shown in Table 5.

TABLE 5

Impurity profiles and respective pH values of voriconazole and 2-hydroxypropyl-β-cyclodextrin formulations prepared using 2-hydroxypropyl-β-cyclodextrin of molar substitution equal to 0.63 dissolved in different buffers with pH value adjusted to 4.7 subjected to stability testing at elevated temperature.

| TESTS | Voriconazole and 2-hydroxypropyl-β-cyclodextrin formulation (MS of 2-HPβCD = 0.63) in Citrate buffer with pH adjusted to 4.7 | | Voriconazole and 2-hydroxypropyl-β-cyclodextrin formulation (MS of 2-HPβCD = 0.63) in Succinate buffer with pH adjusted to 4.7 | | Voriconazole and 2-hydroxypropyl-β-cyclodextrin formulation (MS of 2-HPβCD = 0.63) in Tartrate buffer with pH adjusted to 4.7 | | Voriconazole and 2-hydroxypropyl-β-cyclodextrin formulation (MS of 2-HPβCD = 0.63) in Acetate buffer with pH adjusted to 4.7 | |
|---|---|---|---|---|---|---|---|---|
| | START | 3M 40° C./75% RH IP | START | 3M 40° C./75% RH IP | START | 3M 40° C./75% RH IP | START | 3M 40° C./75% RH IP |
| pH | 4.9 | 5.0 | 4.9 | 5.0 | 5.0 | 5.0 | 5.1 | 5.1 |
| Related substances (%) | | | | | | | | |
| 1-(2,4-difluoro-phenyl)-2-(1H-1,2,4-triazol-1-yl)-ethanone | <LOQ | 1.20 | <LOQ | 1.28 | <LOQ | 0.96 | <LOQ | 1.6 |
| 4-ethyl-5-fluoropyrimidine | <LOQ | 1.26 | <LOQ | 1.35 | <LOQ | 0.95 | <LOQ | 1.6 |
| ((2RS, 3SR)-2-(2,4-difluorophenyl)-3-(pyrimidin-4-yl)-1-(1H-1,2,4-triazol-1-yl)butan-2-ol) | <LOQ | <LOQ | <LOQ | <LOQ | 0.05 | <LOQ | 0.05 | <LOQ |
| (2RS, 3RS)-2-(2,4-Difluorophenyl)-3-(5-fluoropyrimidin-4-yl)-1-(1H-1,2,4-triazol-1-yl)butan-2-ol | <LOQ | 0.23 | <LOQ | 0.23 | <LOQ | 0.27 | <LOQ | 0.13 |
| Total Impurities | 0.07 | 2.7 | 0.07 | 2.9 | 0.10 | 2.2 | 0.05 | 3.4 |

Total impurities = sum of specified and unspecified impurities

When comparing stability testing results presented in Tables 3 & 5 it can be seen that in buffered formulations (pH value in finished product equal to app. 5) containing 2-HPβCD with MS of 0.63, the level of impurities is significantly lower than in the voriconazole formulation containing 2-HPβCD with MS equal to 0.63 dissolved only in ultrapure water. The level of impurities in the later formulation is comparable to the impurities found in the formulation containing 2-HPβCD with MS equal to 0.87.

Example 6

The composition was prepared according to the above described procedure, and as a vehicle ultrapure water was used. pH of formulation was adjusted to 8.5 using 0.1M NaOH prior batch volume make up. The stability of finished product was tested at 40° C./75% RH in inverted position (taken a s a worst case) during 2 weeks. The results are shown in Table 6.

Table 6. Impurity profile and respective pH value of voriconazole and 2-hydroxypropyl-β-cyclodextrin formulation prepared using 2-hydroxypropyl-β-cyclodextrin of molar substitution equal to 0.87 and pH value adjusted to 8.5 with 0.1M sodium hydroxide (NaOH) subjected to 2 weeks stability testing at elevated temperature.

TABLE 6

| TESTS | Formulation: Voriconazole and 2-hydroxypropyl-β-cyclodextrin formulation (MS of 2-HPβCD = 0.87) with pH adjusted to 8.5 using 0.1M NaOH Storage conditions: | |
|---|---|---|
| | START | 2 weeks 40° C./75% RH IP |
| pH | 8.5 | 8.5 |
| Related substances (%) | | |
| 1-(2,4-difluorophenyl)-2-(1H-1,2,4-triazol-1-yl)-ethanone | 0.05 | 0.58 |
| 4-ethyl-5-fluoropyrimidine | 0.05 | 0.65 |
| ((2RS,3SR)-2-(2,4-difluorophenyl)-3-(pyrimidin-4-yl)-1-(1H-1,2,4-triazol-1-yl)butan-2-ol) | <LOQ | <LOQ |
| (2RS,3RS)-2-(2,4-Difluorophenyl)-3-(5-fluoropyrimidin-4-yl)-1-(1H-1,2,4-triazol-1-yl)butan-2-ol | <LOQ | 0.22 |
| Total Impurities | 0.10 | 1.5 |

Total impurities = sum of specified and unspecified impurities

When comparing above presented results to the results of 2 weeks of stability testing at 40° C./75% RH of the formulation prepared in Ultrapure water without additional pH adjustment (see Table 3 for comparison), it can be seen that found level of impurities in formulation with pH above 8.5 is approximately three times higher. This finding implies that voriconazole in the formulation with pH higher than 8 is less stable and degrades in greater extent.

Still, basic formulation (pH above 8.5) prepared with the 2-HPβCD with MS equal to 0.87 is more stable (level of impurities is twice lower) than the formulation with the similar pH formulated with the 2-HPβCD with MS equal to 0.63 (for comparison, see Table 1).

The invention claimed is:

1. A method of stabilizing a lyophilized solid voriconazole formulation, comprising dissolving a substituted β-cyclodextrin characterized by a molar substitution of the β-cyclodextrin by hydroxypropyl groups of more than 0.8 and voriconazole in an aqueous vehicle including no organic solvents to form a dissolved composition, wherein the dissolved composition has pH of 4-7, and lyophilizing the dissolved composition comprising the voriconazole and the substituted β-cyclodextrin characterized by a molar substitution of the β-cyclodextrin by hydroxypropyl groups of more than 0.8 to provide a stabilized lyophilized solid voriconazole formulation, provided that the stabilized lyophilized solid pharmaceutical formulation does not comprise lactose.

2. The method of stabilizing a lyophilized solid voriconazole formulation according to claim 1, wherein the substituent on the β-cyclodextrin is a 2-hydroxypropyl group.

3. The method of stabilizing a lyophilized solid voriconazole formulation according to claim 2, wherein the molar substitution of the 2-hydroxypropyl β-cyclodextrin is 0.8-1.1.

4. The method of stabilizing a lyophilized solid voriconazole formulation according to claim 3, wherein the molar substitution of the 2-hydroxypropyl β-cyclodextrin is 0.8-1.0.

5. The method of stabilizing a lyophilized solid voriconazole formulation according to claim 4, wherein the molar substitution of the 2-hydroxypropyl β-cyclodextrin is 0.9.

6. The method of stabilizing a lyophilized solid voriconazole formulation according to claim 4, wherein the molar substitution of the 2-hydroxypropyl β-cyclodextrin is 0.9.

7. The method of stabilizing a lyophilized solid voriconazole formulation according to claim 1, wherein the dissolved composition further comprises a pH adjusting agent.

8. The method of stabilizing a lyophilized solid voriconazole formulation according to claim 1, wherein the dissolved composition further comprises an acidification agent.

9. The method of stabilizing a lyophilized solid voriconazole formulation according to claim 7, wherein the dissolved composition further comprises one or more organic carboxylic acids.

10. The method of stabilizing a lyophilized solid voriconazole formulation according to claim 1, wherein the dissolved composition further comprises citric, acetic, tartaric and/or succinic acids.

11. The method of stabilizing a lyophilized solid voriconazole formulation according to claim 1, wherein the lyophilized composition comprises 4-10% w/w voriconazole in a solid state.

12. The method of stabilizing a lyophilized solid voriconazole formulation according to claim 11, wherein the lyophilized composition comprises 6% w/w voriconazole in a solid state.

13. The method of stabilizing a lyophilized solid voriconazole formulation according to claim 1, wherein lyophilized the composition comprises about 90-96% w/w β-cyclodextrin in a solid state.

14. The method of stabilizing a lyophilized solid voriconazole formulation according to claim 13, wherein the lyophilized composition comprises about 94% w/w β-cyclodextrin in the solid state.

15. The method of stabilizing a lyophilized solid voriconazole formulation according to claim 2, wherein the lyophilized composition comprises voriconazole and 2-hydroxypropyl-β-cyclodextrin in a molar ratio of up to 1:5.

16. The method of stabilizing a lyophilized solid voriconazole formulation according to claim 2, wherein the said lyophilized composition comprises voriconazole and 2-hydroxypropyl-β-cyclodextrin in a molar ratio of 1:3.6.

17. The method of stabilizing a lyophilized solid voriconazole formulation according to claim 2, wherein the said lyophilized composition comprises voriconazole and 2-hydroxypropyl-β-cyclodextrin in a weight ratio of 1:22 to 1:10.

18. The method of stabilizing a lyophilized solid voriconazole formulation according to claim 17, wherein the lyophilized composition comprises voriconazole and 2-hydroxypropyl-β-cyclodextrin in a weight ratio of 1:18 to 1:14.

19. The method of stabilizing a lyophilized solid voriconazole formulation according to claim 18, wherein the lyophilized composition comprises voriconazole and 2-hydroxypropyl-β-cyclodextrin in a weight ratio of 1:16.

* * * * *